United States Patent [19]

Notte et al.

[11] Patent Number: 5,233,111
[45] Date of Patent: Aug. 3, 1993

[54] CATALYTIC PROCESS FOR SELECTIVE ALKYLATION OF AROMATIC HYDROCARBONS

[75] Inventors: Patrick P. B. Notte, Wavre; Georges M. J. L. Poncelet, Brussels; Marc J. H. Remy, Louvain-La-Neuve; Pierre F. M. G. Lardinois, Lobbes; Marina J. M. Van Hoecke, Brussels, all of Belgium

[73] Assignee: Monsanto Company, St. Louis, Mo.

[21] Appl. No.: 854,941

[22] Filed: Mar. 19, 1992

[30] Foreign Application Priority Data

Mar. 21, 1991 [EP] European Pat. Off. ........... 91870050

[51] Int. Cl.$^5$ .............................................. C07C 2/66
[52] U.S. Cl. ...................................... 585/467; 502/64
[58] Field of Search ........................... 585/467; 502/64

[56] References Cited

U.S. PATENT DOCUMENTS

| | | | |
|---|---|---|---|
| 4,891,448 | 1/1990 | Garces et al. | 568/628 |
| 4,950,817 | 8/1990 | Botta et al. | 570/208 |
| 4,950,832 | 8/1990 | Kojima | 585/463 |
| 4,970,338 | 11/1990 | Matsuda et al. | 562/416 |
| 5,003,120 | 3/1991 | Newman et al. | 585/466 |
| 5,004,841 | 4/1991 | Lee et al. | 585/453 |
| 5,026,940 | 6/1991 | Fellmann et al. | 585/467 |
| 5,026,942 | 6/1991 | Fellmann et al. | 585/466 |

FOREIGN PATENT DOCUMENTS

| | | |
|---|---|---|
| 0288582 | 2/1988 | European Pat. Off. . |
| 0285280 | 5/1988 | European Pat. Off. . |
| 0433932 | 6/1991 | European Pat. Off. . |
| 8803523 | 3/1988 | PCT Int'l Appl. . |
| 9003960 | 4/1990 | PCT Int'l Appl. . |

OTHER PUBLICATIONS

P. C. van Geem et al., "Study of The Transformation of Small-Port into Large-Port Mordenite by Magic Angle Spinning NMR and Infrared Spectroscopy" J. Phys. Chem., 92, (1988) pp. 1585-1589.

N. Y. Chen and F. A. Smith "Preparation of Dealuminized Mordenite" Inorganic Chemistry, vol. 15, No. 2 (1976) pp. 295-297.

F. Raate et al "Comparison Between Small Port and Large Port Mordenites" 1985.

G. S. Lee et al "Shape Selective Alkylation of Polynuclear Aromatics With Mordinite Catalysts: A High Yield Synthesis of 4,4'Diisopropylbiphenyl" Catalyst Letters 2 (1989) pp. 243-248.

Primary Examiner—Anthony McFarlane
Attorney, Agent, or Firm—Lawrence L. Limpus

[57] ABSTRACT

A catalytic process for the selective alkylation of mono- and polycyclic aromatic hydrocarbons is described. The aromatic hydrocarbon is reacted with an alkylating agent in the presence of an acid form of a dealuminated small pore mordenite catalyst having an atomic ratio Si/Al of at least 10:1 to thereby yield the desired alkyl substituted derivative with improved selectivity and improved yield.

17 Claims, No Drawings

CATALYTIC PROCESS FOR SELECTIVE ALKYLATION OF AROMATIC HYDROCARBONS

This invention relates to a process for selective alkylation of aromatic hydrocarbons employing a mordenite zeolite type catalyst.

Alkylated aromatic hydrocarbons are valuable products for the chemical industry. Particularly, dialkylated mono- and polycyclic aromatic hydrocarbon derivatives are of high interest. These compounds have numerous applications in various fields, for example, as solvents for colour formers for carbonless copying paper and as heat transfer fluid. Furthermore, dialkylated aromatic hydrocarbon derivatives constitute a class of intermediates which are highly demanded because these intermediates can be transformed by oxidation into bifunctional reagents, such as e.g. dicarboxylic acids and diols, which are economically very important for the manufacture of many low- and high-molecular weight compounds such as, for example, monomeric-, oligomeric-, and polymeric esters, amides, carbonates and urethanes. The physico-chemical and mechanical properties of these low- and high-molecular weight compounds depend to a large extent on the isomer type as well as on the purity or composition of the isomer mixture of the bifunctional reagent which on its turn is largely dependent on the purity or composition of the isomer mixture of the starting intermediary dialkyl derivative.

An economically convenient way for the manufacture of alkylated mono- and polycyclic aromatic hydrocarbon derivatives consists in the catalytic alkylation of aromatic hydrocarbons with an alkene, alkanol, alkyl halide or any other suitable alkylating agent. The catalytic alkylation processes generally yield a mixture of isomers of alkylated aromatic hydrocarbon derivatives. For a given aromatic hydrocarbon, the type and purity of the alkyl isomer or the composition of the isomer mixture depends on the type of alkylating agent and catalyst, as well as on the reaction conditions used in the alkylation process. Pure isomers of dialkyl mono-or polycyclic aromatic derivatives are economically most attractive, but they are not easily accessible due to the difficulty for separating selected isomers from isomer mixtures by conventional techniques. Accordingly there was a standing desire for making available catalysts which enable the manufacture of selected alkyl substituted aromatic hydrocarbons in high yield and with a good degree of selectivity.

Certain zeolites were found to catalyse the alkylation of aromatic hydrocarbons and various mordenite zeolites are disclosed to catalyse, in a more or less selective way the alkylation of aromatic hydrocarbons.

U.S. Pat. No. 3,140,253 and U.S. Pat. No. 3,367,854 disclose the use of acid-treated mordenite zeolites for the alkylation of monocyclic aromatic hydrocarbons but the control of the number of grafted alkyl groups and of the alkylation sites is rather limited.

U.S. Pat. No. 3,251,897 describes the use of certain crystalline aluminosilicates like rare earth metal exchanged or proton exchanged X and Y zeolites in the alkylation of mono- and polycyclic aromatic hydrocarbons, at temperatures not in excess of 315.5° C. (600° F.).

JP 56-133224 and JP 58-159427 teach the use of acid treated mordenite for the gas phase alkylation of benzene and monoalkyl benzenes to para-dialkylbenzenes.

U.S. Pat. No. 4,361,713 teaches that various zeolite catalysts, like ZSM-5, ZSM-11 and ZSM-12 treated with a halogen-based reactant show improved para-selectivity but poor conversion in the alkylation of benzene and toluene.

EP-A-202 752 teaches the alkylation of polycyclic aromatic hydrocarbons, for example naphthalene, to beta and/or to beta, beta'-isomers with an alkyl aromatic hydrocarbon as alkylating agent in the presence of a crystalline medium pore or large pore acid zeolite optionally containing magnesium and/or phosphorus.

U.S. Pat. No. 4,205,189 teaches the alkylation of mono aromatic hydrocarbons with an alkylating agent in the presence of a zeolite having a silica to alumina mole ratio of at least 12 and a constraint index within the approximate range of 1 to 12. Although reaction conditions can be tuned to higher para- or meta-isomer yields, isomer control is rather limited.

U.S. Pat. No. 4,731,497 teaches the alkylation of monoalkyl substituted benzenes with long chain alpha-olefins in the presence of the acid form of a zeolite having pore sizes between 6.7 and 7.5 Angstroms and having a silica/alumina weight ratio ranging from about 30:1 to 2:1. Alkylation occurs in high yield at the para-position and in about 70% of the reacted product, the benzene ring is attached to the carbon atom at position 2 of the alpha olefin.

JP 56-156222 discloses the alkylation of biphenyl with a silica-alumina or zeolite catalyst to give a monoalkylated biphenyl isomer mixture with a ratio para:-meta-isomer of 3:2.

U.S. Pat. No. 4,480,142 discloses the alkylation of biphenyl using an acid treated montmorillonite to yield 2-ethyl biphenyl as the major reaction product.

Japanese patent publication 3298/(1967) discloses a process for alkylating an aromatic compound with an olefin, alkyl halide or alcohol in the presence of an aluminosilicate such as X zeolite, Y zeolite or mordenite. Alkylation of biphenyl proceeds with low conversion and low p,p'-dialkyl biphenyl selectivity.

U.S. Pat. No. 4,283,573 teaches the reaction of phenolic compounds with reactive derivatives bearing a C6 to C20 alkyl group in the presence of a crystalline zeolite like mordenite to enriched para-alkyl derivatives with the phenolic moiety preferably attached to the 2-position of the alkyl group.

EP-A-288 582 teaches the alkylation of aromatic hydrocarbons with olefins, alcohols or alkyl halides in the presence of a mordenite zeolite catalyst which was treated with a fluorine containing compound. Propylation of biphenyl with propylene is disclosed to proceed selectively to the p,p'-diisopropyl biphenyl in good yield.

EP-A-285 280 discloses the selective para,para'-alkylation of biphenyl with a lower alkene using a mordenite type catalyst or ZSM-5 zeolite catalyst both having a molar ratio of SiO2/Al2O3 of not less than 10.

U.S. Pat. No. 4,891,448 discloses the alkylation of polycyclic aromatic compounds with alkene reagents in the presence of a zeolite catalyst to yield an isomer mixture which is enriched in the para-alkylated isomers. The catalyst used is an acidic mordenite zeolite the crystalline structure of which is, as determined by X-ray diffraction, a matrix of Cmcm symmetry having dispersed therein domains of Cmmm symmetry.

Notwithstanding the availability of many processes and numerous catalysts for the alkylation of aromatic hydrocarbons, there remains a need for an improved catalytic process enabling to carry out the alkylation of aromatic hydrocarbons in smooth conditions, in high yield and with a high degree of number and site selectivity.

It is an object of this invention to provide a catalytic process for the alkylation of aromatic hydrocarbon derivatives to monoalkyl and dialkyl substituted derivatives in high yield and with a controllable selectivity. Another object of this invention is to provide a catalyst which is suitable for use in the said alkylation process.

SUMMARY OF THE INVENTION

It has now been found that an acid form of a dealuminated small pore mordenite having an atomic ratio Si/Al of at least 10:1 is a particularly useful catalyst in the alkylation process of aromatic hydrocarbons. The catalyst combines high alkylating activity with selectivity as to alkylation site and number of the grafted alkyl group(s). This type of catalyst in combination with appropriately selected reaction conditions enables to direct the alkylation to produce desired siteisomers, and in particular to produce dialkyl substituted derivatives from mono- and polycyclic aromatic hydrocarbons with improved selectivity and improved yield.

In one aspect, this invention relates to a process for the selective alkylation of an aromatic hydrocarbon by reacting the aromatic hydrocarbon with an alkylating agent in the presence of a mordenite zeolite catalyst to thereby yield the desired alkyl derivative wherein the catalyst is an acid form of a dealuminated small pore mordenite having an atomic ratio Si/Al of at least 10:1.

In another aspect, this invention relates to the use of an acid form of a dealuminated small pore mordenite, having an atomic ratio Si/Al of at least 10:1, as catalyst in the selective alkylation reaction of mono- and polycyclic aromatic hydrocarbons.

DETAILED DESCRIPTION OF THE INVENTION

The aromatic hydrocarbon according to the invention is a mono- or polycyclic aromatic hydrocarbon of formula I $$(Ar^1-X-Ar^2)_n-Ar^3 \quad (I)$$

wherein
$Ar^1$, $Ar^2$ and $Ar^3$ may represent, independently from each other, a non-substituted or substituted monocyclic or fused or non-fused polycyclic aromatic group,
$Ar^3$ may also represent hydrogen,
X can be absent or represent an oxygen atom, a sulphur atom, a carbonyl group, a sulfonyl group or a C1-C4 alkylene group,
n can be zero or 1, and, when n is zero, $Ar^3$ is different from hydrogen and $(Ar^1-X-Ar^2)_n$ is hydrogen.

Preferably, the monocyclic and/or fused or non-fused polycyclic aromatic group is a phenyl, a 1,1'-biphenyl, a p-terphenyl, a naphthyl, a fluorenyl or an anthracenyl group, each group being optionally substituted by one or more substituents selected from a halogen, a hydroxy group, a C1-C6 alkoxy group, a C1-C4 alkoxycarbonyl group, or a C1-C20 alkyl group which itself may be substituted by a halogen, a hydroxy, a C1-C4 alkoxy, a carboxy or a C1-C4 alkoxycarbonyl radical, and wherein at least one para- or meta-position of the monocyclic aromatic group, or at least one of the corresponding positions in the non-fused or fused polycyclic aromatic group is unsubstituted.

Preferred derivatives of formula I are the ones wherein $Ar^1$ and $Ar^2$ are both phenyl and $Ar^3$ is phenyl, naphthyl or hydrogen, and wherein each phenyl and the naphthyl group may be substituted by one or two groups independently selected from a halogen, a hydroxy group, a C1-C6 alkoxy group, a carboxy group, a C1-C4 carboxyalkyl group, or a C1-C12 alkyl group which is optionally substituted by a halogen, a hydroxy, a carboxy or a C1-C6 alkoxy group, X is absent or is an oxygen atom and n is zero or 1, and wherein $Ar^3$ is different from hydrogen and $(Ar^1-X-Ar^2)_n$ is hydrogen when n is zero.

Preferred arommatic hydrocarbons of formula I include benzene, C1-C12 alkyl benzene, biphenyl, mono C1-C12 alkylphenyl benzene, p-terphenyl, diphenyl ether, 1,4-diphenoxy benzene, and naphthalene which may be substituted or not by one or two C1-C12 alkyl groups.

The most preferred derivatives of formula I are biphenyl, ethyl benzene, p-terphenyl, naphthalene and diphenyl ether, in particular biphenyl.

Alkylating agents according to the invention comprise C2-C20 alkenes, C2-C20 polyolefins, C4-C7 cycloalkenes, C1-C20 alkanols, C1-C20 alkyl halides and C1-C20 alkyl aromatic hydrocarbons. Typical alkylating agents are C2-C12 alkenes, C1-C12 alkanols, C1-C12 alkyl halides and C1-C12 alkyl benzene derivatives, such as for example, ethylene, propylene, 1-butene, 2-butene, isobutene, 1-pentene, 2-pentene, 1-hexene, 2-hexene, 1-octene, 1-decene, 1-dodecene, methanol, ethanol, 1-propanol, 2-propanol, 1-butanol, 2-butanol, 2-methyl-1-propanol, 2-methyl 2-propanol, 1-pentanol, 1-hexanol, 1-octanol, 1-decanol, 1-dodecanol, and C1-C12 alkyl chloride, C1-C12 alkyl bromide and C1-C12 alkyl iodide such as e.g. methyl chloride, methyl bromide, methyl iodide, ethyl chloride, 1-chloropropane, 2-chloropropane, 2-bromopropane, 1-butyl chloride, 2-pentyl chloride, 2-pentyl bromide, 1-hexyl chloride, 2-hexyl chloride, 2-hexyl bromide, 1-octyl chloride, 1-decyl chloride, 1-dodecyl chloride, and diisopropyl benzenes.

Preferred alkylating agents are C2-C6 alkenes, C1-C6 alkyl halides and C1-C6 alkanol derivatives. More preferred are the C3-C4 alkene and C3-C4 alkanol derivatives, in particular propene, 1-butene, 2-butene, isobutene, 1-propanol, 2-propanol, 1-butanol, 2-butanol and 2-methyl 2-propanol.

The most preferred alkylating agents are propene, isobutene, 2-propanol and 2-butanol, particularly propene and 2-propanol.

The essential catalyst for use in the alkylation process of the invention is prepared from a small pore mordenite. A mordenite is an aluminosilicate which generally has an atomic Si/Al ratio of about 5:1. Its structure and properties are described in Zeolite Molecular Sieves, by D. W. Breck at pages 122 to 124 and 162 to 163 (J. Wiley, 1974). The crystalline structure consists in a series of tetraedrons based on $SiO_4$ and $AlO_4$. Their organization results in two types of channels: one defined by eight-membered rings with free apertures of 2.9×5.7 Angstroms and a second one defined by twelve-membered rings with free apertures of 6.7×7 Angstroms along the c-axis. There are two types of mordenites which can be distinguished by their adsorption properties: the large pore mordenites, which adsorb molecules like benzene with a kinetic diameter of about 6.6 Angstroms, and the small pore mordenites, natural as well as synthetic ones, which only adsorb smaller molecules with a kinetic diameter of about 4.4 Angstroms. The diffusion limitation existing in small pore mordenites may be due to the presence of amorphous material in this channel system, to the nature of the cations, and/or to the presence of crystal stacking defaults in the c-direction of the mordenite. Mordenites are also characterized by morphological differences: large pore mordenites generally appear as spherulites whereas small pore mordenites generally appear as rods.

These characteristics of the small pore mordenites are described by F. Raatz et al. in J. Chem. Soc. Faraday Trans 1, 79, 2299 to 2309 (1983); by P. C. van Geem et al. in J. Phys. Chem, 92, 1585 to 1589, (1988) and by D. W. Breck in Zeolite Molecular Sieves on pages 122 to 125, (J. Wiley—1974).

The catalyst for use according to the invention is prepared from a small pore mordenite zeolite containing as cations alkaline or alkaline earth metal ions or ammonium ions, and which may be prepared by known techniques.

The starting small pore mordenite is preferably an alkaline metal containing mordenite, most preferably a sodium containing mordenite. The preparation technique is described, for example, in French patent 1411753. Such starting small pore mordenites are commercially available, for example as ZM-060 mordenite from La Grande Paroisse, (France).

Such preferred mordenite has narrowly defined crystallographic properties. The mordenite has a crystalline structure, as determined by conventional X-ray diffraction, which contains a majority of domains of Cmcm symmetry and which is substantially free of domains of Cmmm symmetry. By the term "which contains a majority" is meant that the crystalline structure is composed of generally more than 90%, preferably more than 95% and most preferably more than 99% of domains of Cmcm symmetry. By the term "substantially free" is meant that no domains of Cmmm symmetry are detectable in the mordenite by conventional X-ray diffraction. This means that the level of possible domains of Cmmm symmetry in the mordenite is less than 0.5%, most preferably less than 0.01%. This starting sodium mordenite has a symmetry index of 0.7 and is present in major part in the form of aggregates composed of rods. The rods have a mean length of about 50000 Angstroms with a hexagonal section of a mean width of about 10000 Angstroms and a mean height of about 3000 Angstroms.

Generally these rods form aggregates with dimensions ranging from about 1 to 1000 microns, typically ranging from about 1 to 100 microns. The aggregate dimensions have been assessed using a Sympatec Laser Particle Analyzer after dispersion of the mordenite in water by use of an ultrasonic bath. X-ray diffraction spectra have been made using a Siemens D-500 equipment and using the K alpha 1 line of copper as a reference.

The unit cell of this mordenite has the following elementary formula $Na_7Al_7Si_{40}O_{94}.24H_2O$. The atomic Si/Al ratio is between 4.5 and 6.5, typically close to 6. The sodium level for the dried mordenite is between 4 and 6.5% by weight, typically about 5.3% by weight. Silicon, aluminium and sodium levels have been obtained by Inductively Coupled Plasma Emission Spectroscopy using a Philips PV8490 equipment with an argon plasma operated between 6000 and 11000 degrees Kelvin.

The starting small pore mordenite described above does not adsorb benzene or biphenyl in a significant amount. Typically this mordenite has a sorption capacity for biphenyl of about 0.01 to 0.02 g per g of mordenite zeolite, calculated on the dried mordenite. Biphenyl sorption is conducted by submitting the mordenite at 200° C. to a helium stream saturated in biphenyl until the mordenite is saturated as assessed by flame ionization detection of the biphenyl in the helium stream downstream of the sorption vessel.

The mordenite suitable for use as catalyst in the alkylation process according to the invention is an acid form of a dealuminated small pore mordenite which is prepared by dealumination of a small pore mordenite zeolite.

Dealumination of a zeolite is a process leading to a zeolite with a higher atomic Si/Al ratio. It may generally be carried out by isomorphous replacement of the aluminium atoms present in the crystalline network by e.g. silicon atoms, or by extraction of the aluminium atoms without their replacement in the crystalline framework. Isomorphous replacement can for example be conducted by exposing the mordenite to $SiCl_4$ vapors at high temperature. According to the extraction technique aluminium can be extracted from the catalyst framework by treatment with a mineral or organic acid or treatment with a complexing agent. Typically the extraction is carried out on a sodium or ammonium mordenite. Hydrothermal treatment followed up by acid leaching is another process to dealuminate mordenites which is generally carried out on ammonium mordenites. Still another way to extract aluminium atoms from the mordenite framework is to conduct, preferably on an ammonium mordenite, a thermal treatment followed up by acid leaching. In general dealumination is carried out by subjecting the starting zeolite once or more times to a treatment according to one of the said dealumination techniques, or to a combination of treatments according to the said techniques.

The mordenite suitable for use as catalyst according to the invention is preferably dealuminated by one or more combined hydrothermal and acid treatments. These combined treatments are preferably carried out on the ammonium or proton form of the small pore mordenite.

Typically, the catalyst suitable for use according to the invention can be prepared from a sodium small pore mordenite by a combined treatment which comprises the following sequential steps:

a. exchange of the sodium ions by ammonium ions or protons,
b. thermal treatment in the presence of steam (referred to hereafter interchangeably as "steaming" or "hydrothermal" treatment),
c. treatment with an aqueous acid solution.

Typically, the catalyst is prepared as follows:

a. Sodium ions in the starting mordenite are exchanged by ammonium ions by treatment of the mordenite with an aqueous solution of an ionizable ammonium salt, preferably ammonium nitrate or ammonium acetate, of a molarity generally superior to 0.5 at a temperature generally between about 20° C. and about 150° C.

Optionally this cation exchange may be repeated in combination or not with an intermediate wash with water.

Optionally sodium ions extraction can be carried out by treatment of the starting mordenite with a diluted mineral or organic acid.

Generally the remaining sodium content, calculated on the dried catalyst is less than 1% by weight, preferably less than 0.5%, typically less than 0.1%.

b. Thermal treatment is carried out by heating the ammonium mordenite or proton mordenite obtained in step a for at least 10 minutes at a temperature generally between about 300° C. and about 900° C. in the presence of an atmosphere containing at least about 1% steam. Preferably the mordenite is treated at a temperature between 400° C. and 800° C. for at least 20 minutes in an atmosphere containing at least about 5% steam. The treatment can also be carried out by the so-called self steaming technique which comprises calcination of the mordenite in a confined atmosphere, as well as by any other convenient calcination technique known in the art. The atmosphere generally comprises, apart from steam, a conventional gas or gas mixture, known in the art, the components of which do not have any poisoning or undesirable effect on the mordenite. Suitable gases and gas mixtures are for example, nitrogen, helium and air.

During the hydrothermal treatment ammonium ions are decomposed to thereby yield a protonic (acid) form of the mordenite.

c. The calcined mordenite from step b is then subjected to an acid treatment which comprises contacting the mordenite with an aqueous acid solution, preferably with an aqueous solution of a mineral acid.

Preferably this treatment is done by stirring the mordenite in a solution of a strong mineral acid generally of a normality between about 0.1N and 12N for at least 10 minutes at a temperature between about 20° C. and about 150° C., and more preferably between about 80° C. and 150° C.

Before subsequent drying, typically carried out between about 80° C. and about 150° C., the mordenite may be washed once or several times with an aqueous acid solution and/or water.

Optionally the thermal treatment in the presence of steam followed up by acid treatment may be repeated once or several times. Optionally the last acid treatment may be followed up by a thermal treatment in the absence of added steam typically carried out at a temperature comprised between about 400° C. and about 700° C.

As a result of the hydrothermal treatment aluminium atoms are expelled from the crystalline framework of the catalyst and generally deposited in the porous system. During the subsequent acid treatment most of the aluminium species are dissolved and removed from the catalyst. By the combined hydrothermal and acid treatments the amount of aluminium species removed is generally more than 50% of the total aluminium content, preferably more than 80%, more preferably more than 90%. The extent of the aluminium species removal can be controlled by the dealumination conditions. This dealumination treatment increases the atomic ratio Si/Al from its typical original value, being close to 6, to an atomic ratio Si/Al of at least 10:1. The mordenites for use according to the invention generally have an atomic Si/Al ratio between 20:1 and 1000:1, preferably between 30:1 and 200:1, more preferably between 60:1 and 150:1, and most preferably between 80:1 and 120:1.

It is to be understood that the atomic Si/Al ratio is an overall ratio based on the total amounts of silicon and aluminium in the mordenite (frame work plus extra frame work), and that the atomic ratio Si/Al of the crystalline matrix (frame work) may differ significantly, and reach ratios higher than 1000:1.

During the dealumination process according to the above described combined treatment the porosity of the small pore mordenite catalyst is significantly modified. After removal of about 20% of the aluminium atoms from the crystalline framework by the combined steaming and acid treatments, the porous system is unblocked and larger molecules like e.g. biphenyl can be sorbed in the porous system of the catalyst. The unblocking of the porous system allowing free diffusion of molecules of a kinetic diameter of about 6.6 Angstroms such as biphenyl is a sign of the modifications which occur to the porous system.

The porous system of small pore mordenites generally comprises microporous (radius from about 3 to 15 Angstroms), mesoporous (radius from about 15 to 1000 Angstroms) and macroporous (radius above 1000 Angstroms) components. By the unblocking, new pores are also created as shown by the increase of the mesoporous and macroporous volumes after the combined treatment of the starting sodium small pore mordenite.

Typically biphenyl adsorption will have increased as a result of the combined hydrothermal and acid treatment from about 0.016 g per g of mordenite up to between 0.05 and 0.12 g per g of mordenite, calculated on the dried catalyst. The porous volumes can be calculated by methods known in the art and described for example by S. Lowell in Introduction to Powder Surface Area (J. Wiley, 1979). Typically, the acid form of the dealuminated small pore mordenite suitable for use according to this invention will have a porous system such that the ratio of the meso- plus macroporous system to the total porous system of the mordenite zeolite will be comprised between 0.2 and 0.5.

The characteristics of typical mordenite catalysts for use according to the invention, are as follows:

an acid form, i.e. a form wherein substantially all cations are protons, an atomic Si/Al ratio from about 20:1 to about 200:1, a symmetry index from about 0.7 to about 2.6, a biphenyl sorption capacity from about 0.05 to about 0.12 g per g of catalyst, calculated on a dried basis.

a ratio of mesoporous plus macroporous volumes to total porous volume comprised between 0.2 and 0.5, a crystalline structure which is a matrix of Cmcm symmetry substantially free of Cmmm symmetry, appearance in the form of aggregates composed of rods.

The symmetry index has been obtained from the X-ray diffraction spectrum of the mordenite zeolite. It is defined as the sum of the peak height of the (111) and (241) reflections divided by the peak height of the (350) reflection. It is typically between 0.5 and 0.8 for the starting small pore mordenite and is typically comprised between 0.7 and 2.6 after the above dealumination treatment.

Optionally the small pore sodium, ammonium or proton mordenite before or after the steaming treatment or the acid treatment may be reduced in size using methods known in the art like e.g. crossed air jet milling. In the preparation of the catalyst used in the Examples described hereinafter this operation has been carried out with an Alpine Aeroplex 200 AFG equipment. The dimensions of size reduced catalysts generally range from about 0.1 to about 1000 microns, and typically from about 0.1 to about 100 microns. Most preferred sizes range from 0.1 to 10 microns.

The mordenites may be used as a catalyst according to the invention in any suitable form known in the art, as such e.g. directly in the form of a powder, or in combination with or without a suitable support and/or binder known in the art, in the form of e.g. powder, extrudates, pellets, tablets, granules, spheres, and the like. Such support and binder materials may be inert or may have an intrinsic catalytic activity which is compatible with the catalytic activity of the mordenite catalyst. Examples of such materials are e.g. oxides like alumina, silica, magnesia and silica-alumina; charcoal, kieselguhr, and various clays. The form of the catalyst for use in the alkylation process of the invention may be prepared according to techniques which are well known in the art.

In the alkylation process according to the invention virtually any weight ratio of catalyst to aromatic hydrocarbon can be used but practically it is limited by the conversion rate which may not become unacceptably slow. The weight ratio catalyst: aromatic hydrocarbon is generally kept between about 1:1000 and 1:0,1, preferably between 1:500 and 1:1, more preferably between 2:100 and 1:10, most preferably about 5:100.

The ratio of alkylating agent: aromatic hydrocarbon may vary according to the number of alkyl groups which are to be grafted on the aromatic hydrocarbon, the nature of the alkylating agent as well as of the aromatic hydrocarbon, the catalyst and the reaction conditions such as e.g. temperature, pressure, reaction time and type of reactor. In general, however, the mole ratio of alkylating agent: aromatic hydrocarbon is kept between 0.5 and 5 per alkyl group to be grafted on the aromatic hydrocarbon, typically between 0.7 and 2, and preferably about 1:1.

The alkylation process according to the invention can be carried out in any batch-type or continuous-type alkylation reactor known in the art, such as for example a fixed bed, slurry bed or fluidized bed reactor, a countercurrent reactor and the like. The alkylation can be carried out with the alkylating agent and/or the aromatic hydrocarbon in the liquid or gas phase, or the aromatic hydrocarbon or alkylating agent can act as a solvent for the other, or optionally a solvent which remains inert under the reaction conditions can be used. Furthermore the aromatic hydrocarbon can be brought in contact with the required amount of alkylating agent at once at the beginning of the reaction, or gradually as the reaction proceeds.

The optimum reaction temperature and pressure depend on the other reaction conditions, on the nature of the aromatic hydrocarbon and on the alkylating agent, as well as on the nature of the desired reaction product. Typically the reaction temperature is kept between about 100° C. and about 400° C., preferably between about 150° C. and about 300° C.

The alkylation process can generally be carried out at a pressure ranging from about 1 kPa to about 4000 kPa, typically between about 10 kPa and 1000 kPa, preferably between about 10 kPa and 500 kPa.

The optimum time during which the aromatic hydrocarbon and the alkylation agent are brought in contact in the presence of the catalyst depends largely on the nature of the aromatic hydrocarbon, on the alkylating agent, on the catalyst, on the reactor type, on the other reaction conditions and on the desired reaction product. The reaction time can vary largely from a few seconds to a few hours. The optimal reaction time can easily be determined by the skilled person according to known techniques.

The products obtained by the process according to the invention include a mixture of alkylated mono- or polycyclic aromatic hydrocarbons of various isomers of which the alkylated isomer distribution can be controlled and tuned towards higher levels of the desired para- or linear isomers as well as towards higher levels of meta- or kinked isomers by selection of the appropriate reaction conditions.

The para- or linear alkylated isomers are those in which the alkyl group(s) is (are) attached at the extremities of an aromatic hydrocarbon molecule such as to provide a product which has the smallest critical diameter.

The meta- or kinked isomers are those in which at least one alkyl group is attached in a meta- or equivalent position of the aromatic hydrocarbon. The latter molecules have larger critical diameters in comparison with the para- or linear alkylated isomers.

In the alkylation of biphenyl, for example, a para-alkylated product is para,para'-diisopropyl biphenyl, and a meta-alkylated product is meta,para'-diisopropyl biphenyl. In the alkylation of naphthalene, for example, a linear alkylated product is 2,6-diisopropyl naphthalene, and a kinked alkylated product is 2,7-diisopropyl naphthalene.

For a given aromatic hydrocarbon the appropriate reaction conditions for optimal production of a selected alkylated aromatic hydrocarbon isomer or isomer mixture are selected according to standard techniques of the art. Selection may be made for example, by evaluation of the evolution of the composition of the reaction product (e.g. analysed by gas-chromatography (GC) or GC-mass spectrometry) which is obtained in test runs wherein one or more reaction parameters, such as for example temperature and pressure were varied. The examples 4 to 19 below are illustrative of the fact that the alkylated isomer distribution can be controlled and tuned towards a selected isomer/isomer mixture.

In the alkylation process of biphenyl with propylene according to the invention the reaction temperature, when keeping the other reaction conditions substantially the same, is for example most preferably kept between 175° C. and 220° C. when the desired reaction product is para,para'-diisopropyl 1,1'-biphenyl and between 200° C. and 275° C. when the desired product is meta, para'-diisopropyl 1,1'-biphenyl.

Alkylation of an aromatic hydrocarbon to selective isomers will, for the purpose of this invention, be qualified by the conversion of the starting hydrocarbon, the selectivity towards the desired isomer and by the yield of such isomer as obtained in the crude alkylation product. Conversion refers to the mole percentage of the starting aromatic hydrocarbon which has been converted in the alkylation reaction.

In the alkylation according to the invention conversion can vary widely depending on the aromatic hydrocarbon, on the alkylating agent, on the reaction temperature and on the pressure, on the catalyst preparation, as well as on the mode of operation e.g. continuous- or batch-operation. For batch operations conversion will be at least superior to 5%, typically at least 30%, preferably at least 50% and most preferably at least 70%.

Selectivity to a given alkylated isomer is the mole percentage of the starting aromatic hydrocarbon which has been converted to that desired isomer. Selectivity can also be expressed based on a product family, e.g. as mole percentage of a particular dialkylated isomer on the total amount of dialkylated isomers formed. In the reaction of biphenyl with propene the crude reaction product will, depending on the reaction conditions and the catalyst, contain alkylates rich in the para,para'-dialkyl isomer, or rich in the meta,para'-dialkyl isomer or rich in a mixture of meta,para'- and meta,meta'- dialkyl isomers. Typically in the process of the invention the selectivity to one specific dialkyl isomer in the dialkylated biphenyl family ranges from about 20 mole percent to about 90 mole percent.

In the process of this invention the selectivity to specific dialkylated isomers calculated based on the dialkylated product family is at least 20 mole percent, preferably at least 30 mole percent, most preferably at least 50 mole percent. The yield in any particular isomer in the crude alkylated aromatic hydrocarbon represents the numerical product of conversion times selectivity.

The following examples are given to illustrate the catalysts and the process of this invention and should not be construed as limiting its scope. All percentages, unless otherwise stated, are expressed in mole percent. Unless otherwise stated the term "added pressure" means the pressure of alkylating agent which is superimposed at the onset of the reaction, to the pressure of the reaction mixture at the set reaction temperature. The value of the "added pressure" is maintained throughout the duration of the reaction.

The starting mordenite is a small pore sodium or ammonium mordenite produced, respectively, as ZM-060 and ZM-101 by La Grande Paroisse, France.

Examples 22 to 26 and 29 to 31 are comparative and given to illustrate the unique catalytical properties of the catalysts according to the invention. The examples illustrate that the alkylation process of aromatic hydrocarbons proceeds poorly or not at all when an acid form of a non-dealuminated small pore mordenite is used as catalyst and proceeds with less selectivity and yield when an acid form of a dealuminated small pore mordenite is employed in the preparation of which the dealumination has been carried out without steaming (hydrothermal) treatment.

EXAMPLE 1

Catalyst preparation

ZM-060 small pore sodium mordenite is converted to the ammonium form by treatment with an aqueous solution of ammonium nitrate as follows: 400 g of the sodium mordenite are contacted with 1 liter of an aqueous solution containing 100 g of ammonium nitrate. The mixture is stirred at 60° C. for 4 hours. The ammonium mordenite formed is recovered by filtration and washed with demineralized water till pH 7. The ammonium mordenite is subjected to an hydrothermal treatment at atmospheric pressure in a horizontal furnace swept by an air current at a rate of 250N liters per hour. The temperature is increased gradually to 680° C. at a rate of 150° C. per hour. Steam is introduced in the air from about 300° C. The steam level is adjusted by means of a saturator. Water flow is close to 80 g per hour. After a period of 5 hours at 680° C. under these conditions the furnace heating is turned off and at 300° C. the steam flow is stopped. The mordenite is then treated at 90° C. with a 6N aqueous nitric acid solution for 3 hours under vigorous stirring. The catalyst is separated by filtration and washed twice with deionized water at 70° C. The solid is finally dried at 150° C. for 10 hours. Analysis of the catalyst gives the following results: an atomic Si/Al ratio of 100:1; a total pore volume of 0.328 ml/g; a symmetry index of 1.68; a ratio of meso plus macro porosity over the total porosity of 0.33.

EXAMPLE 2

Catalyst preparation

ZM-060 small pore mordenite is converted to the ammonium form by treatment with an aqueous solution of ammonium nitrate as described in Example 1. The ammonium mordenite is then subjected to an hydrothermal treatment at atmospheric pressure in an horizontal rotating tubular furnace which is heated at 560° C. and operated on a continuous basis. The ammonium mordenite is continuously fed to the rotary furnace and contacted at this high temperature with steam. The furnace operations are tuned so as to provide a one hour residence time for the mordenite in the high temperature zone. Water is fed to the furnace at a rate corresponding to 80 g water per hour as measured at 25° C. The mordenite is then treated in a static furnace, at atmospheric pressure, swept by an air current at a rate of 250N liters per hour. The temperature is progressively increased to 680°-700° C. at a rate of 150° C./hour. Steam is introduced in the air from about 300° C. Its level is adjusted by means of a saturator. Water flow is close to 80 g/hour.

After a period of 4 hours between 680°-700° C. under these conditions the furnace heating is stopped, and at 300° C. the steam flow is stopped. The mordenite is then treated with a 6N aqueous nitric acid for 3 hours at 90° C. under vigorous stirring. The catalyst is recovered by filtration and washed twice with deionized water at 70° C., then once with a 1N aqueous nitric acid at 60° C. and finally with deionized water at 70°. The mordenite is then dried at 150° C. for 10 hours. Analysis of this catalyst gives the following results: atomic Si/Al ratio of 80:1; a total pore volume of 0.257 ml/g; a symmetry index of 1.63; a ratio of meso plus macro porosity over total porosity of 0.35.

EXAMPLE 3

Catalyst preparation

ZM-060 small pore sodium mordenite is fed to an Alpine Aeroplex 200 AFG equipment operated with an introduction pressure of $5.10^5$ Pa at room temperature at an approximate throughput of 4 kg/hour. The particle selector was operated at about 11000 rotations per minute so as to obtain a mordenite size ranging from about 0.9 to 6 microns. This size reduced mordenite was submitted first to an ammonium exchange as described in Example 1, then to a first hydrothermal treatment carried out at 620° C. in an horizontal rotating tubular furnace and then to an acid treatment as described in Example 2. The mordenite is then subjected to a second hydrothermal treatment carried out between 680°-700° C., followed by a second acid treatment and a final drying step as described in Example 2. Analysis of this catalyst gives the following results: atomic Si/Al ratio of 90:1; a total pore volume of 0.303 ml/g; a symmetry index of 1.61; a ratio of meso plus macro porosity over total porosity of 0.40.

EXAMPLE 4

Alkylation of ethylbenzene-para selectivity

Ethylbenzene (700 g) and the catalyst from example 1 (35 g or 5% by weight on ethylbenzene) are contacted with propylene at a temperature of 160° C. with an added propylene pressure of $0.8 \times 10^5$ Pa for 2 liter Parr pressure autoclave operated under agitation. Analysis of the reaction mixture by gas chromatography gives a conversion of 79.6%, a yield in meta-isopropyl ethyl benzene of 20.6%, a yield in para-isopropyl ethyl benzene of 54.5%. The sum of the mono-isopropyl ethylbenzene isomers represents 95.4% of the total conversion. The selectivity to the para-isopropyl ethyl benzene is 68.5% and the selectivity to the meta-isopropyl ethylbenzene is 25.9%.

EXAMPLE 5

Alkylation of ethylbenzene-meta selectivity

Ethylbenzene (700 g) and the catalyst from example 2 (35 g or 5% by weight on ethylbenzene) are contacted with propylene at a temperature of 250° C. with an added pressure of propylene of $0.3 \times 10^5$ Pa for 5 hours in a 2 liter Parr pressure autoclave operated under agitation. Analysis of the reaction mixture by gas chromatography gives a conversion of 95.1%, a yield in meta-isopropyl ethylbenzene of 49.7%, a yield of para-isopropyl ethylbenzene of 33.1%. The sum of the mono-isopropyl ethylbenzene isomers represents 88.3% of the total conversion. The selectivity to the para-isopropyl ethylbenzene is 34.8% and the selectivity to the meta-isopropyl ethylbenzene is 52.3%.

EXAMPLE 6

Alkylation of 1,1'-biphenyl-para selectivity 1,1'-biphenyl (80 g) and the catalyst from example 3 (4 g or 5% by weight on the biphenyl) are contacted with propylene at a temperature of 250° C. with an added pressure of propylene of $1 \times 10^5$ Pa for 6 hours in a 300 ml Parr pressure autoclave operated under agitation. Analysis of the reaction mixture by gas chromatography gives a conversion of 93.5%, a yield in para,para'-diisopropyl biphenyl of 65%, a yield in meta,para'-diisopropyl biphenyl of 12.7%. The sum of the diisopropyl biphenyl products represents 84.2% of the total conversion. The selectivity to the para,para'-diisopropyl biphenyl is 69.5% and the selectivity to the meta,para'-diisopropyl biphenyl is 13.6%.

EXAMPLE 7

Alkylation of 1,1'-biphenyl-para selectivity 1,1'-biphenyl (800 g) and the catalyst from example 1 (40 g or 5% by weight on the biphenyl) are contacted with propylene at a temperature of 200° C. with an added pressure of propylene of $0.8 \times 10^5$ Pa for 6 hours in a 2 liter Parr pressure autoclave operated under agitation. Analysis of the reaction mixture by gas chromatography gives a conversion of 62.4%, a yield in para,para'-diisopropyl biphenyl of 34.2%, a yield in meta,para'-diisopropyl biphenyl of 6.7%. The sum of the diisopropyl biphenyl products represents 66.1% of the total conversion. The selectivity to the para,para'-diisopropyl biphenyl is 54.7% and the selectivity to the meta, para'-diisopropyl biphenyl is 10.7%.

EXAMPLE 8

Alkylation of 1,1'-biphenyl-para selectivity 1,1'-biphenyl (800 g) and the catalyst from example 1 (40 g or 5% by weight on the biphenyl) are contacted with propylene at a temperature of 250° C. with an added pressure of propylene of $7 \times 10^5$ Pa for 5 hours in a 2 liter Parr pressure autoclave operated under agitation. Analysis of the reaction mixture by gas chromatography gives a conversion of 87.0%, a yield in para,para'-diisopropyl biphenyl of 40.5%, a yield in meta,para'-diisopropyl biphenyl of 20.2%. The sum of the diisopropyl biphenyl products represents 72.7% of the total conversion. The selectivity to the para,para'-diisopropyl biphenyl is 46.6% and the selectivity to the meta,para'-diisopropyl biphenyl is 23.2%.

EXAMPLE 9

Alkylation of 1,1'-biphenyl-para selectivity 200 mg of the catalyst from example 1 were introduced in a glass microreactor placed in an oven at 200° C. This catalytic bed is contacted at 200° C. with a stream of helium containing $1,6.10^3$ Pa 1,1'-biphenyl and $4.10^4$ Pa propylene. The total flow rate of the gaseous mixture is 36 ml/min and the biphenyl W.H.S.V. (weight hourly space velocity) is 1.2 g of biphenyl per hour and per gram of catalyst. Gas chromatography analysis of the reaction mixture after a period of 70 minutes indicates a conversion of 36.7%, a yield in para,para'-diisopropyl biphenyl of 20.5%, a yield in meta,para'-diisopropyl biphenyl of 3.3%. The sum of the diisopropyl biphenyl products represents 66.5% of the total biphenyl conversion. The selectivity to the para,para'-diisopropyl biphenyl is 55.8% and the selectivity to the meta,para'-diisopropyl biphenyl is 9.0%.

EXAMPLE 10

Alkylation of 1,1'-biphenyl-meta selectivity 1,1'-biphenyl (800 g) and the catalyst from example 1 (40 g or 5% by weight on the biphenyl) are contacted with propylene at a temperature of 250° C. with an added pressure of propylene of $0.8 \times 10^5$ Pa for 6 hours in a 2 liter Parr pressure autoclave operated under agitation. Analysis of the reaction mixture by gas chromatography gives a conversion of 93.6%, a yield in para,para'-diisopropyl biphenyl of 11.4%, a yield in meta,para'-diisopropyl biphenyl of 35.4% and a yield in meta,meta'-diisopropyl biphenyl of 8.0%. The sum of the diisopropyl biphenyl products represents 59.8% of the total conversion. The selectivity to the para,para'-diisopropyl biphenyl is 12.2%, the selectivity to the meta,para'-diisopropyl biphenyl is 37.8% and the selectivity to the meta,meta'-diisopropyl biphenyl is 8.5%.

EXAMPLE 11

Alkylation of 1,1'-biphenyl-meta selectivity 1,1'-biphenyl (800 g) and the catalyst from example 1 (40 g or 5% by weight on the biphenyl) are contacted with propylene at a temperature of 275° C. with an added pressure of propylene of $0.2 \times 10^5$ Pa for 6 hours in a 2 liter Parr pressure autoclave operated under agitation. Analysis of the reaction mixture by gas chromatography gives a conversion of 94.1%, a yield in para,para'-diisopropyl biphenyl of 8.2%, a yield in meta,para'-diisopropyl biphenyl of 26.9% and a yield in meta,meta'-diisopropyl biphenyl of 17.1%. The sum of the diisopropyl biphenyl products represents 57.4% of the total conversion. The selectivity to the para,para'-diisopropyl biphenyl is 8.7%, the selectivity to the meta,para'-diisopropyl biphenyl is 28.6% and the selectivity to the meta,meta'-diisopropyl biphenyl is 18.2%.

EXAMPLE 12

Alkylation of 1,1'-biphenyl-meta selectivity.

1,1'-Biphenyl (800 g) and the catalyst from example 1 (40 g or 5% by weight on the biphenyl) are contacted with propylene at a temperature of 200° C. with an added pressure of propylene of $0.2 \times 10^5$ Pa for 5 hours in a 2 liter Parr pressure autoclave operated under agitation. Analysis of the reaction mixture by gas chromatography gives a conversion of 92.2%, a yield in para,-para'-diisopropyl biphenyl of 11.3%, a yield in meta,-para'-diisopropyl biphenyl of 32.0% and a yield in meta,meta'-diisopropyl biphenyl of 11.0%. The sum of the diisopropyl biphenyl products represents 60.0% of the total conversion. The selectivity to the para,para'-diisopropyl biphenyl is 12.3%, the selectivity to the meta,para'-diisopropyl biphenyl is 34.6% and the selectivity to the meta,meta'-diisopropyl biphenyl is 11.9%.

EXAMPLE 13

Alkylation of 1,1'-biphenyl-meta selectivity 200 mg of the catalyst from example 1 were introduced in a glass microreactor placed in an oven at 200° C. This catalytic bed is contacted at 200° C. with a stream of helium containing $1,6.10^3$ Pa of 1,1'-biphenyl and $8.10^3$ Pa of isopropanol. The total flow rate of the gaseous mixture is 36 ml/min and the biphenyl W.H.S.V. (weight hourly space velocity) is 1.2 g of biphenyl per hour and per gram of catalyst. Gas chromatography analysis of the reaction mixture after a period of 70 minutes gives a conversion of 59.3%, a yield in para,para'-diisopropyl biphenyl of 9.8%, a yield in meta,para'-diisopropyl biphenyl of 26.4% and a yield in meta,meta'-diisopropyl biphenyl of 5.3%. The sum of the diisopropyl biphenyl products represents 70% of the total biphenyl conversion. The selectivity to the para,para'-diisopropyl biphenyl is 16.5%, the selectivity to the meta,para'-diisopropyl biphenyl is 44.5% and the selectivity to the meta,meta'-diisopropyl biphenyl is 8.9%.

EXAMPLE 14

Alkylation of diphenyl ether-para selectivity

Diphenyl ether (800 g) and the catalyst from example 1 (40 g or 5% by weight on the diphenyl ether) are contacted with propylene at a temperature of 225° C. with an added pressure of propylene of $1 \times 10^5$ Pa for 5 hours in a 2 liter Parr pressure autoclave operated under agitation. Analysis of the reaction mixture by gas chromatography gives a conversion of 76.6%, a yield in para,para'-diisopropyl diphenyl ether of 35.3%, a yield in meta,para'-diisopropyl diphenyl ether of 16.5%. The sum of the diisopropyl diphenyl ether products represents 69.6% of the total conversion. The selectivity to the para,para'-diphenyl ether is 46.0% and the selectivity to the meta,para'-diisopropyl diphenyl ether is 21.5%.

EXAMPLE 15

Alkylation of diphenyl ether-meta selectivity

Diphenyl ether (80 g) and the catalyst from example 1 (4 g or 5% by weight on the diphenyl ether) are contacted with propylene at a temperature of 250° C. with an added pressure of propylene of $0.8 \times 10^5$ Pa for 5 hours in a 300 ml Parr pressure autoclave operated under agitation. Analysis of the reaction mixture by gas chromatography gives a conversion of 92.4%, a yield in para,para'-diisopropyl diphenyl ether of 27.5%, a yield in meta, para'-diisopropyl diphenyl ether of 36.0%. The sum of the diisopropyl diphenyl ether products represents 74.8% of the conversion. The selectivity to the para,para'-diphenyl ether is 29.7% and the selectivity to the meta,para'-diisopropyl diphenyl ether is 39.0%.

EXAMPLE 16

Alkylation of naphthalene-linear selectivity.

Naphthalene (80 g) and the catalyst from example 1 (4 g or 5% by weight on the naphthalene) are contacted with propylene at a temperature of 220° C. with an added pressure of propylene of $0.8 \times 10^5$ Pa for 3 hours in a 300 ml Parr pressure autoclave operated under agitation. Analysis of the reaction mixture by gas chromatography gives a conversion of 89.0%, a yield in the 2,6-diisopropyl naphthalene of 34.4% and a yield in 2,7-diisopropyl naphthalene of 11.8%. The sum of the diisopropyl naphthalene represents 51.7% of the conversion. The selectivity to the 2,6-diisopropyl naphthalene is 38.7% and the selectivity to the 2,7-diisopropyl naphthalene is 13.3%.

EXAMPLE 17

Alkylation of naphthalene-kinked selectivity.

Naphthalene (800 g) and the catalyst from example 2 (40 g or 5% by weight on the naphthalene) are contacted with propylene at a temperature of 250° C. with an added pressure of propylene of $0.8 \times 10^5$ Pa for 1 hour 30 minutes in a 2 liter Parr pressure autoclave operated under agitation. Analysis of the reaction mixture by gas chromatography gives a conversion of 82.3%, a yield in the 2,6-diisopropyl naphthalene of 15.0% and a yield in 2,7-diisopropyl naphthalene of 9.4%. The sum of the diisopropyl naphthalene represents 32.5% of the conversion. The selectivity to the 2,6-diisopropyl naphthalene is 18.2% and the selectivity to the 2,7-diisopropyl naphthalene is 11.5%.

EXAMPLE 18

Alkylation of 1,1'-biphenyl-para selectivity.

Biphenyl (80 g) and the catalyst from example 1 (4 g or 5% by weight on biphenyl) are contacted with 1-butene at a temperature of 225° C. with an added pressure of 1-butene of $1.1 \times 10^5$ Pa for 8 hours in a 300 ml Parr pressure autoclave operated under agitation. Analysis of the reaction mixture by gas chromatography gives a conversion of 79.7%, a yield in para,para'-diisobutyl biphenyl of 43.9%, a yield in meta, para'-diisobutyl biphenyl of 6.8%. The sum of the diisobutyl biphenyl represents 64.3% of the total conversion. The selectivity to the para,para'-diisobutyl biphenyl is 55.0% and the selectivity to the meta,para'-diisobutyl biphenyl is 8.5%.

EXAMPLE 19

Alkylation of 1,1'-biphenyl-meta selectivity.

Biphenyl (80 g) and the catalyst from example 1 (4 g or 5% by weight on biphenyl) are contacted with 1-butene at a temperature of 250° C. with an added pressure of 1-butene of $1.1 \times 10^5$ Pa for 7 hours in a 300 ml Parr pressure autoclave operated under agitation. Analysis of the reaction mixture by gas chromatography gives a conversion of 86.9%, a yield in para,para'-diisobutyl biphenyl of 17.9%, a yield in meta, para'-diisobutyl biphenyl of 19.4%. The sum of the diisobutyl biphenyl represents 45.2% of the total conversion. The selectivity to the para,para'-diisobutyl biphenyl is 20.6% and the selectivity to the meta,para'-diisobutyl biphenyl is 22.3%.

EXAMPLE 20

Catalyst preparation

ZM-060 small pore sodium mordenite is treated with ammonium nitrate as in example 1 to exchange the sodium by ammonium cations. The catalyst is dealuminated by thermal treatment carried out in presence of steam as in example 1, this treatment is carried out at 620° C. for 5 hours. After cooling the catalyst is treated at 90° C. with 6N aqueous nitric acid under vigorous stirring for 3 hours. The catalyst is separated by filtration and washed twice with deionized water at 70° C. The solid is finally dried at 150° C. for 10 hours. Analysis of the catalyst gives the following results: atomic Si/Al ratio of 50:1; a symmetry index of 1.85; a total pore volume of 0.32 ml/g; a ratio meso plus macro porosity over the total porosity of 0.422.

EXAMPLE 21

Catalyst preparation

Catalyst from example 20 is further dealuminated by thermal treatment carried out in the presence of steam as in example 1, this treatment is carried out at 700° C. for 5 hours. After cooling the catalyst is treated at 110° C. with 8N aqueous nitric acid under vigorous stirring for 4 hours. The catalyst is separated by filtration and washed twice with deionized water at 70° C. The solid is finally dried at 150° C. for 10 hours. Analysis of the catalyst gives the following results: atomic Si/Al ratio of 150:1; a symmetry index of 2.18; a total pore volume of 0.31 ml/g; a ratio meso plus macro porosity over the total porosity of 0.45.

COMPARATIVE EXAMPLE 22

Catalyst preparation

ZM-060 small pore sodium mordenite is converted to the acidic form by treatment with 1N aqueous hydrochloric acid as follows: 20 g of the sodium small pore mordenite are contacted for thirty minutes with 200 ml of 1N aqueous hydrochloric acid at room temperature under vigorous stirring. The hydrogen mordenite formed is recovered by filtration and washed with demineralized water till pH 7. The recovered solid is dried in air at 100° C., heated at 700° C. in a flow of air for 2 hours and then cooled to room temperature. The mordenite is treated with a 6N aqueous nitric acid under reflux for 2 hours under vigorous stirring. The catalyst is recovered by filtration and washed with demineralized water till pH 7. Analysis of the catalyst gives the following results: atomic Si/Al ratio of 10:1; a symmetry index of 1.58, a total pore volume of 0.216 ml/g, a ratio of meso plus macro porosity of 0.18. Before its use the catalyst is activated by heating in air at 700° C. for 2 hours.

COMPARATIVE EXAMPLE 23

Catalyst preparation

ZM-101 small pore ammonium mordenite is heated for 2 hours at 700° C. in a flow of air, then cooled to room temperature. The mordenite is then treated with a 6N aqueous nitric acid solution under reflux for 2 hours under vigorous stirring. The catalyst is recovered by filtration and then washed with demineralized water till pH 7. Analysis of the catalyst gives the following results: atomic Si/Al ratio of 20:1; a symmetry index of 1.5; a total pore volume of 0.285 ml/g; a ratio of meso plus macro porosity over total porosity of 0.42. Before its use, the catalyst is activated by heating in air at 700° C. for 2 hours.

COMPARATIVE EXAMPLE 24

Alkylation of 1,1'-Biphenyl

Biphenyl (80 g) and the catalyst from example 22 (1.6 g or 2% by weight on biphenyl) are contacted with propylene at a temperature of 250° C. at a total pressure of $8.2 \times 10^5$ Pa for 4 hours in a 300 ml Parr pressure autoclave operated under agitation. Analysis of the reaction mixture by gas chromatography gives a conversion of 2.15% and a yield in para,para'-diisopropyl biphenyl of 0.1%. The sum of the diisopropyl biphenyl derivatives represents 7.3% of the total conversion. The selectivity to the para,para'-diisopropyl biphenyl is 5.48%.

COMPARATIVE EXAMPLE 25

Alkylation of 1,1'-Biphenyl

Biphenyl (80 g) and the catalyst from example 23 (1.6 g or 2% by weight on biphenyl) are contacted with propylene at a temperature of 250° C. at a total pressure of $8.2 \times 10^5$ Pa for 4 hours in a 300 ml Parr pressure autoclave operated under agitation. Analysis of the reaction mixture by gas chromatography gives a conversion of 36.0%, a yield in para,para'-diisopropyl biphenyl of 4.9%, a yield in meta,para'-diisopropyl biphenyl of 0.7%. The sum of the diisopropyl biphenyl derivatives represents 16.6% of the total conversion. The selectivity to the para,para'-diisopropyl biphenyl is 13.7% and the selectivity to the meta,para'-diisopropyl biphenyl is 2.1%.

COMPARATIVE EXAMPLE 26

Alkylation of 1,1'-Biphenyl

Biphenyl (80 g) and the catalyst from example 22 (4 g or 5% by weight on biphenyl) are contacted with propylene at a temperature of 250° C. with an added pressure of propylene of $5 \times 10^5$ Pa for 4 hours in a 300 ml Parr pressure autoclave operated under agitation. Analysis of the reaction mixture by gas chromatography gives a conversion of 5.6% and a yield in para,para'-diisopropyl biphenyl of 0.2%. The sum of the diisopropyl biphenyl represents 4.7% of the total conversion. The selectivity to the para,para'-diisopropyl biphenyl is 3.5%.

EXAMPLE 27

Alkylation of 1,1'-Biphenyl

Biphenyl (80 g) and the catalyst from example 20 (4 g or 5% by weight on biphenyl) are contacted with propylene at a temperature of 200° C. with an added pressure of propylene of $0.8 \times 10^5$ Pa for 4 hours in a 300 ml Parr pressure autoclave operated under agitation. Analysis of the reaction mixture by gas chromatography gives a conversion of 33.4%, a yield in para,para'-diisopropyl biphenyl of 12.0%, a yield in meta, para'-diisopropyl biphenyl of 1.3%. The sum of the diisopropyl biphenyl represents 40.8% of the total conversion. The selectivity to the para,para'-diisopropyl biphenyl is 35.9% and the selectivity to the meta,para'-diisopropyl biphenyl is 3.9%.

EXAMPLE 28

Alkylation of 1,1'-Biphenyl

Biphenyl (80 g) and the catalyst from example 21 (4 g or 5% by weight on biphenyl) are contacted with propylene at a temperature of 200° C. with an added pressure of propylene of $0.8 \times 10^5$ Pa for 4 hours in a 300 ml Parr pressure autoclave operated under agitation. Analysis of the reaction mixture by gas chromatography gives a conversion of 8.0%, a yield in para,para'-diisopropyl biphenyl of 1.3%, a yield in meta, para'-diisopropyl biphenyl of 0.1%. The sum of the diisopropyl biphenyl represents 18.5% of the total conversion. The selectivity to the para,para'-diisopropyl biphenyl is 16.2% and the selectivity to the meta,para'-diisopropyl biphenyl is 1.7%.

COMPARATIVE EXAMPLE 29

Catalyst preparation

ZM-101 small pore ammonium mordenite, atomic ratio Si/Al of 5.8:1, is heated progressively to 600° C. at a rate of 150° C./hour for 4 hours in a static furnace swept by an air current. Analysis of the solid obtained after cooling shows that the catalyst is in the acid form.

COMPARATIVE EXAMPLE 30

Alkylation of 1,1'-biphenyl

Biphenyl (80 g) and the catalyst from example 29 (4 g or 5% by weight on biphenyl) are contacted with propylene at a temperature of 200° C. with an added propylene pressure of $0.8 \times 10^5$ Pa for 5 hours in a 300 ml Parr pressure autoclave operated under agitation. Analysis of the reaction mixture by gas chromatography gives a conversion of 0.4%, a yield in meta, para'-diisopropyl biphenyl of 0.02% and a yield in para, para'-diisopropyl biphenyl of 0.05%.

COMPARATIVE EXAMPLE 31

Alkylation of 1,1'-biphenyl 200 mg of the catalyst from example 29 are introduced in a glass microreactor placed in an oven at 200° C. This catalytic bed is contacted at 200° C. with a stream of helium containing $1.6 \times 10^3$ Pa 1,1'-biphenyl and $6 \times 10^4$ Pa propylene. The total flow rate of the gaseous mixture is 36 ml/min and the biphenyl W.H.S.V. (Weight Hourly Space Velocity) is 1.2 g of biphenyl per hour and per gram of catalyst. Gas chromatography analysis of the reaction mixture after a period of 70 minutes indicates a conversion of 1.6% and a yield in mono-isopropyl biphenyl of 1.6%. No diisopropyl biphenyl are detected.

We claim:

1. A process for the selective dialkylation of a polycyclic aromatic hydrocarbon by reacting the aromatic hydrocarbon with an alkylating agent in the presence of a zeolite catalyst to thereby yield the alkyl substituted derivative, characterized in that the catalyst is an acid form of a dealuminated small pore mordenite having an atomic Si/Al ratio of at least 10:1.

2. The process of claim 1 wherein the mordenite catalyst is in the form of aggregates of rods, having an atomic Si/Al ratio of 20:1 to 1000:1, a symmetry index from 0.7 to 2.6, a biphenyl sorption capacity from 0.05 to 0.12 g per g of catalyst, calculated on the dried catalyst, and a ratio of mesoporous plus macroporous volumes to total porous volume comprised between 0.2 and 0.5.

3. The process of claim 2 wherein the catalyst has an atomic Si/Al ratio between 80:1 to 120:1.

4. The process of claim 1 wherein the catalyst is prepared by dealumination of a small pore mordenite carried out by one or more combined hydrothermal and acid treatments.

5. The process of claim 1 wherein the catalyst is prepared from a small pore sodium mordenite by a treatment which comprises the following sequential steps:
    (a) exchange of the sodium ions by ammonium ions or protons,
    (b) thermal treatment in the presence of steam, and
    (c) treatment with an aqueous acid solution.

6. The process of any one of claims 1, 2, 3 or 5 wherein the aromatic hydrocarbon is a polycyclic aromatic hydrocarbon of formula I

$$(Ar^1—X—Ar^2)_n—Ar^3 \qquad\qquad I$$

wherein $Ar^1$, $Ar^2$ and $Ar^3$ represent, independently from each other, a non-substituted or substituted monocyclic-or fused or nonfused polycyclic aromatic group, and $Ar^3$ also represents hydrogen, X is absent or represents an oxygen atom, a sulphur atom, a carbonyl group, a sulfonyl group or a C1–C4 alkylene group; n is zero or 1, and wherein, when n is zero, $Ar^3$ is different from hydrogen and from a monocyclic aromatic group and $(Ar^1—x—Ar^2)_n$ is hydrogen.

7. The process of any one of claims 1, 2, 3 or 5 wherein in the aromatic hydrocarbon of formula I $Ar^1$ and $Ar^2$ are both phenyl and $Ar^3$ is phenyl, naphtyl or hydrogen, and wherein the naphthyl and each phenyl group is optionally substituted by one or two groups independently selected from a halogen, a hydroxy group, a C1–C6 alkoxy group, a carboxy group, a C1–C4 carboxyalkyl, or a C1–C12 alkyl group which is optionally substituted by a halogen, a hydroxy, a carboxy or a C1–C6 alkoxy group, X is absent or is an oxygen atom and n is zero or 1, and wherein $Ar^3$ is different from hydrogen and from a monocyclic aromatic group and $(Ar^1—x—Ar^2)_n$ is hydrogen when n is zero.

8. The process of any one of claims 1, 2, 3 or 5 wherein the aromatic hydrocarbon of formula I is biphenyl, p-terphenyl, diphenyl ether or naphthalene.

9. The process of any one of claim 1, 2, 3 or 5 wherein the alkylating agent is a C2-C20 alkene, C2-C20 polyolefin, C4–C7 cycloalkene, C1-C20 alkanol, C1-C20 alkyl halide or a C1-C20 alkyl aromatic hydrocarbon.

10. The process of any one of claims 1, 2, 3 or 5 wherein the alkylating agent is a C2-C6 alkene, C1-C6 alkyl halide or C1-C6 alkanol.

11. The process of any one of claims 1, 2, 3 or 5 wherein biphenyl is dialkylated with propylene.

12. The process according to any of claims 1, 2, 3 or 5 wherein the catalyst is further characterized by a crystalline structure, as determined by X-ray diffraction, which contains a majority of domains of Cmcm symmetry and which is substantially free of domains of Cmmm symmetry.

13. A method for the selective dialkylation of a polycyclic aromatic hydrocarbon comprising alkylating the hydrocarbon in the presence of an acid form of a dealuminated small pore mordenite having an atomic Si/Al ratio between 20:1 and 1000:1, a symmetry index of 0.7 to 2.6, a biphenyl sorption capacity from 0.05 to 0.12 g per g catalyst, calculated on the basis of dried catalyst weight, and a ratio of mesoporous plus macroporous volumes to total porous volume between 0.2 and 0.5.

14. The method of claim 13 wherein the dealumination has been carried out by one or more combined hydrothermal and acid treatments.

15. The method of claim 14 wherein the catalyst has an atomic Si/Al ratio between 80:1 and 120:1, the aromatic hydrocarbon is ethylbenzene, biphenyl, p-terphenyl, naphthalene or diphenyl ether and the hydrocarbon is alkylated with an alkylating agent wherein the alkylating agent is a C2–C20 alkene, a C1–C20 alkyl aromatic hydrocarbon, a C1–C20 alkyl halide or a C1–C20 alkanol.

16. The method of claim 15 wherein the aromatic hydrocarbon is biphenyl and the alkylating agent is propylene or 2-propanol.

17. The method according to any one of claims 13–16 wherein the mordenite is further characterized by a crystalline structure which, as defined by X-ray diffraction, contains a majority of domains of Cmcm symmetry and which is substantially free of domains of Cmmm symmetry.

* * * * *